(12) United States Patent
Tilley

(10) Patent No.: US 7,520,910 B2
(45) Date of Patent: Apr. 21, 2009

(54) MODULAR AIR PURIFICATION UNIT

(75) Inventor: Greg A. Tilley, Monkton, MD (US)

(73) Assignee: TVi Corporation, Glenn Dale, MD (US)

( * ) Notice: Subject to any disclaimer, the term of this patent is extended or adjusted under 35 U.S.C. 154(b) by 340 days.

(21) Appl. No.: 11/299,803

(22) Filed: Dec. 12, 2005

(65) Prior Publication Data

US 2006/0230730 A1     Oct. 19, 2006

Related U.S. Application Data

(60) Provisional application No. 60/635,187, filed on Dec. 10, 2004.

(51) Int. Cl.
  *B01D 45/00* (2006.01)
  *B01D 46/00* (2006.01)
(52) U.S. Cl. .................................. 55/471; 55/350.1
(58) Field of Classification Search ............ 55/279, 55/471, 350.1
  See application file for complete search history.

(56) References Cited

U.S. PATENT DOCUMENTS

| | | | |
|---|---|---|---|
| 2,390,297 A * | 12/1945 | Gilmore | 55/492 |
| 3,487,624 A * | 1/1970 | Tignanelli | 55/482 |
| 4,028,817 A * | 6/1977 | Winstel | 34/86 |
| 4,236,902 A | 12/1980 | Fricke | |
| 4,773,922 A * | 9/1988 | Ross et al. | 55/481 |
| 5,167,681 A | 12/1992 | O'Keefe et al. | |
| 5,417,729 A | 5/1995 | Greenleaf, Sr. | |
| 6,050,774 A | 4/2000 | LeBaron | |
| 6,808,547 B2 * | 10/2004 | Ota et al. | 55/478 |
| 2004/0118093 A1 * | 6/2004 | Chang et al. | 55/471 |

OTHER PUBLICATIONS

Aller Air Industries, Model I-6500, product flyer, May 10, 2004.
Aller Air Industries, Model I-6500 A-HO, product flyer, Jun. 10, 2004.
Aller Air Industries, Model I-6500 HU, product flyer.
Website pages from http://members.fortunecity.com listing specifications for Aller Air Industrial air purifiers.

* cited by examiner

*Primary Examiner*—Walter D Griffin
*Assistant Examiner*—Amber Orlando
(74) *Attorney, Agent, or Firm*—Whiteford, Taylor & Preston LLP; Jeffrey C. Maynard; Gregory M. Stone

(57) ABSTRACT

A modular air filtration unit having a disposable filter section separable from an inlet cap and a blower section. The modular air filtration unit is of rugged, lightweight construction and eases the interchange of used filter assemblies without jeopardizing leakage that might cause contamination of the intended clean environment.

10 Claims, 2 Drawing Sheets

MODULAR AIR PURIFICATION UNIT

CROSS REFERENCE TO RELATED APPLICATION

This application is based upon and claims benefit of co-pending U.S. Provisional Patent Application Ser. No. 60/635,187 entitled "Modular Air Purification Unit", filed with the U.S. Patent and Trademark Office on Dec. 10, 2004 by the inventor herein, the specification of which is incorporated herein by reference.

BACKGROUND OF THE INVENTION

1. Field of the Invention

This invention relates to filtration units, and more particularly to a modular system easing the interchange of disposable filters in an air filtration unit.

2. Background of the Prior Art

Hospital administrators struggle with the creation of hospital infrastructure necessary to manage and contain infectious disease outbreaks. In the current infectious disease threat environment, occurrences of SARS, West Nile Virus, etc. have raised awareness of the need for infrastructure that can contain pathogens in an isolated environment so as not to risk infecting other patients or hospital workers attempting to treat an infected patient. Likewise, with increased threat of attacks using biological agents, hospitals need to be prepared to handle a potential outbreak of a contagious disease brought on by a biological attack. Most hospitals, however, lack appropriate isolation and filtration equipment to ensure a safe environment. The equipment that is available to provide clean, filtered air to what is intended to be a "clean" environment requires service, including replacement of filter members. Generally, such servicing requires breaking factory seals, and risks leaving gaps in what is intended to be the replacement sealing members that, in turn, could lead to an inadvertent spread of the pathogen that the filter assembly is intended to contain.

Likewise, in the current environment of heightened risk of terror attacks, emergency response personnel and administrations have realized that a very real need exists for providing methods and equipment to be able to respond to attacks involving chemical, biological, radiological, and/or nuclear weapons. In the event of such an attack, it is essential that emergency response personnel be able to establish a treatment center, a command center, and the like in what may be an environmentally hostile, and potentially lethal, environment. Of course, to do so, it is necessary that such personnel either be individually suited against the dangerous environment, or be located in a shelter that shields them from such environment. In the latter case, if the shelter must be located in a contaminated area but requires that persons spend extended amounts of time in the shelter, it is often impractical to supply each such person with their own self-contained air supply. Rather, as a practical matter, it would likely be necessary to filter air from outside of the shelter, and provide such filtered air to the closed environment inside of the shelter. Obviously, it is essential that the air be filtered to the greatest degree possible, as in the event of a biological attack, even minute amounts of contaminant making its way into the shelter could be deadly to the occupants.

Furthermore, in the event of such an attack, it may be necessary to establish an on-site isolation ward so that persons who are suspected of having been exposed to a dangerous contagion can be isolated from the general population, but may still be treated by emergency response personnel. In this case, it is necessary to ensure that any air escaping such shelter to the uncontaminated exterior is sufficiently filtered so as to ensure that such contaminants do not reach the general population.

Air filtration systems have been provided in the past that attempt to provide for filtration of particulate matter, bacteria, viruses, and the like. Such air filtration systems often take the form of a vertical steel cabinet having an air intake chamber at the bottom, one or more filters above the intake chamber through which the contaminated air is intended to pass, a motor-driven blower assembly above the filters, and a clean air discharge outlet. The types of filters provided are selected based on the environment in which the system is intended to be used. Notably, however, in highly toxic or dangerous environments, it would become necessary to change the filter after extended use. Unfortunately, changing the filter necessarily involves reseating a new filter against the appropriate sealing surfaces inside of the cabinet. While, during assembly in a controlled factory environment, a tight seal can be monitored and, through careful manufacturing procedures, can be created with relative confidence, replacing a filter assembly in a potentially hostile environment in the field does not provide such confidence. Notably, if an environment has been infected with a biological agent (which again may require very minute amounts of contagion to jeopardize the life of persons in the area), any leakage of air around the filter can be deadly. During the process of reseating a filter, a gap of only the size of a human hair can allow a sufficient number of partials of a biological contaminant into or out of the intended "clean" area that would jeopardize the health of the area's occupants. Thus, it is imperative that even in the field environment, the ability to establish a complete seal between the filter and its enclosure is maintained after a filter is replaced.

Moreover, filters and cabinet structures are typically certified by skilled technical personnel as having met a particular performance standard, i.e., as being capable of filtering particular pathogens at a given concentration over a given amount of time. While a filter may be tested at the manufacturing facility to confirm its ability to filter the intended contaminants, certification of the filter alone is meaningless if it is placed in a cabinet that allows flow of contaminated air around the filter. Likewise, certification of a cabinet without including the filter in the analysis is meaningless if gaps exist between the filter and housing that would allow contaminated air to pass. As there is currently no certification standard for the combined system of a cabinet with a filter in this area, there is urgent need to provide a combined filter and cabinet assembly that ensures a complete seal between the filter and cabinet even after a used or contaminated filter has been replaced in a hospital or in the field.

Additionally, the CDC requires monitoring the pressure in the room or shelter to which the filter is attached in order to maintain pressure in a specified band. Alarm and Warning set points allow visual and audible notification to the user when the pressure has deviated from the required operation window. Furthermore, data logging of the pressure, continuous or only on an alarm, can be used by risk management for a record of activity from the room or shelter.

SUMMARY OF THE INVENTION

It is, therefore, an object of the present invention to provide an air purification system that avoids the disadvantages of the prior art.

It is another object of the present invention to provide an air purification system having modular construction. It is a related object of the present invention to enable an air purification system having a disposable filter assembly. It is a further related object of the present invention to enable an air purification system that is easy to assemble and disassemble.

It is a further object of the present invention to enable monitoring of the pressure in a room or shelter to which such air purification system is attached. It is a related object of the present invention to enable a system to continuously record data associated with the monitored pressure. It is a further related object of the present invention to enable a system to record data associated with the monitored pressure, upon indication of an alarm condition.

The various features of novelty that characterize the invention will be pointed out with particularity in the claims of this application.

BRIEF DESCRIPTION OF THE DRAWINGS

The above and other features, aspects, and advantages of the present invention are considered in more detail, in relation to the following description of embodiments thereof shown in the accompanying drawings, in which.

DETAILED DESCRIPTION

The invention summarized above and defined by the enumerated claims may be better understood by referring to the following description, which should be read in conjunction with the accompanying drawings. This description of an embodiment, set out below to enable one to build and use an implementation of the invention, is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
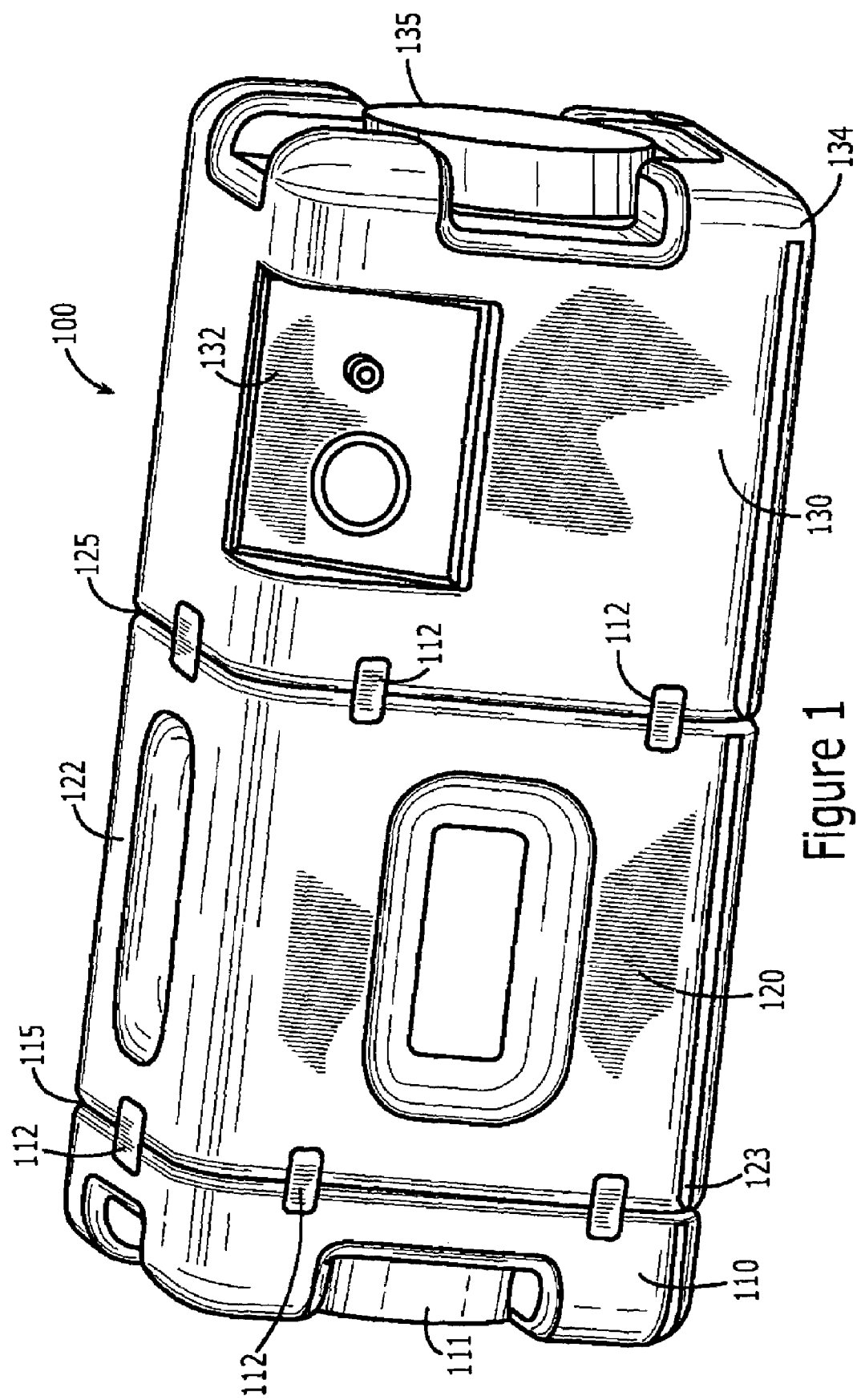
FIG. 1 is an illustration of an air purification unit according to an embodiment of the present invention.

In an effort to avoid the above-described disadvantages, a portable, modular air purification unit is provided. As shown in FIG. 1, the modular air purification unit according to a first preferred embodiment is shown generally at 100, and comprises an inlet section 110, a filter section 120, and a blower section 130. Inlet section 110 is provided an inlet coupling 111 configured to receive a flexible hose or other conduit, or alternately to simply serve as an open inlet to the filter assembly. Inlet coupling 111 may be integrally formed with, embedded in, or otherwise rigidly and sealingly attached to the body of inlet section 110, which preferably is formed of plastic or other lightweight, inexpensive material. One or more clamp members 112 are preferably provided that, when tightened, pull inlet section 110 towards filter section 120 along seam 115. Preferably, a free end of inlet section 110 intended for mating with filter section 120 is configured with an interface to tightly fit with the inlet end of filter section 120. Thus, when inlet section 110 is so connected to filter section 120, a tight seal exists that will prevent most contaminants from entering the air purification unit 100 through seam 115. Nonetheless, as the seam 115 is positioned upstream of the filter assembly, and because a lower pressure condition exists inside of inlet section 110 and filter section 120 than outside of unit 100, any leakage would occur in the form of outside air flowing into the unit 100 before the filter section 120, ensuring that any such leakage air is filtered before being exhausted from blower section 130. In an alternate embodiment, the filter section 120 can be constructed of a single unit with the inlet section 110 and inlet coupling 111 fully integrated in a single shell.

Filter section 120 comprises a rigid outer shell 122, preferably formed of plastic or other inexpensive, lightweight material. Inside of the rigid outer shell 122 is a rigid filter assembly 200 (FIG. 2) of standard construction, selected for the threat/contagion environment in which the unit 100 is intended to be used. Such filter assembly 200 may be configured to filter dust, chemicals, gases, biological agents, etc., as is known in the art. The interior of filter section 120 is preferably provided a ledge at a first end 123, such as the end adjacent inlet section 110, configured to support the base of such filter assembly 200. When positioned vertically, filter assembly 200 may be dropped into filter section 120, and when so positioned (with minimal clearance between the filter frame and the interior edges of the end walls of filter section 120), a bead of urethane (or other flexible sealing material) is applied to the seam between the interior edges of filter section 120 and the end walls of the filter assembly, such that the only available flow path through filter section 120 is through the filter assembly 200. As the filter is intended as a disposable unit, and the outer shell 122 of filter section 120 is formed of an inexpensive, generally lightweight material such as plastic, the entire filter section 120 may simply be disposed of and replaced when it comes time to replace the filter. In this way, a new filter assembly 200 having the factory seal between the frame of the filter and the shell 122 can be assured with each new filter application.

Blower section 130 likewise comprises a rigid outer shell 134 formed of lightweight, inexpensive material, and is connected to filter section 120 along seam 125. Seam 125 is preferably formed with the same construction as seam 115 to ensure a tight seal between filter section 120 and blower section 130. The exhaust end of blower section 130 comprises an outlet coupling 135 configured to receive a flexible hose or other conduit, or alternately to simply serve as an open outlet from the air purification unit 100. Outlet coupling 135 may be integrally formed with, embedded in, or otherwise rigidly and sealingly attached to the body of blower section 130. Internal to blower section 130 is preferably a motor driving a blower unit, comprising at least a fan that is positioned with respect to a fan coupling 210 (FIG. 2), such that the plane of differential pressure on either side of the fan is no further downstream than the free end 213 of the fan coupling 210.

Figure 2:
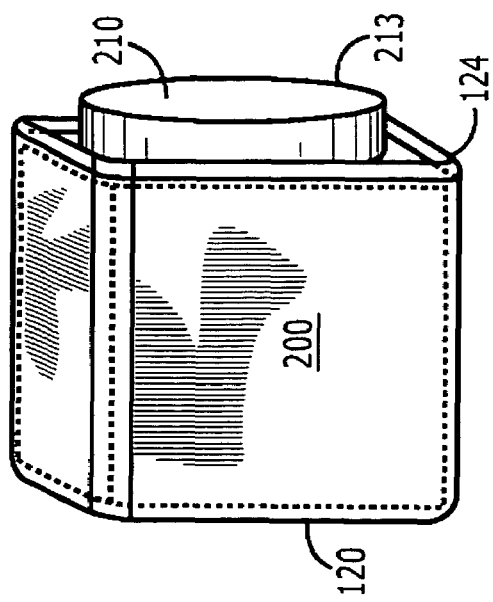
FIG. 2 is an illustration of filter assembly according to an embodiment of the present invention.

As shown in FIG. 2, the filter assembly 200 (shown in phantom) is provided inside of filter section 120. Filter assembly 200 is preferably provided a fan coupling 210 extending away from the second end 124 of filter section 120 and into blower section 130 when the unit 100 is fully assembled. Fan coupling 210 is preferably configured such that when filter section 120 is joined to blower section 130 the plane of the pressure differential at the fan is no further downstream than the free end 213 of the fan coupling 210. In this manner, the air surrounding the fan coupling 210 is at the higher pressure of the differential pressures on either side of the fan, which higher pressure is at least greater than the pressure outside of the blower unit. Given this assembly, even in the event of an imperfect seal between the fan coupling 210 and the blower section 130, the risk of leakage of contaminated air through the seam 125 between the filter section 120 and the blower section 130 is eliminated, as the pressure differential between the inside of the modular blower unit 100 and outside of the blower unit will cause any leakage to flow from inside the unit 100 (which air has already passed through and been cleaned by filter section 120) to outside the unit.

Figure 3:
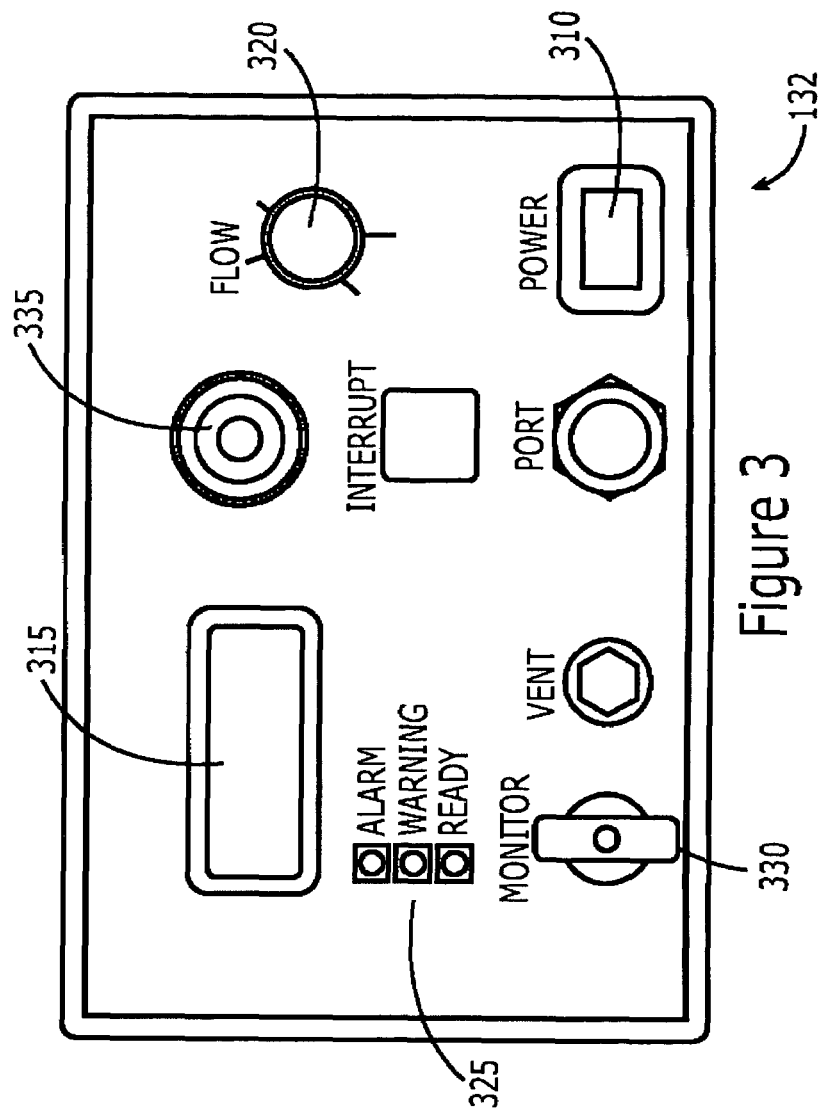
FIG. 3 is an illustration of a control panel for the air purification unit of FIG. 1.

Referring to FIG. 3, a control panel 132 accessible from the exterior of blower section 130 allows monitoring and adjustment of the fan housed inside of blower section 130. An on/off switch 310 may be provided. The control panel may also optionally provide a pressure indicator 315 for the airflow through filter section 120. Control 320 enables manual adjustment of the speed of the fan. Operating indicating lights 325 provide a visual indication of the system condition. Optionally, the control panel 132 may enable monitoring of the pressure in an attached room or shelter by connecting an appropriate detector to a monitor input 330. Such remote pressure monitoring also enables logging of data as selected by the user. Data logging can be accomplished based upon specific time intervals or upon specific events, such as an alarm condition, such events to be determined by the user. An alarm condition may be revealed by visual indication 325 or by an audible alarm 335. In some embodiments, the data logger may be internal to the unit or may be connected to a remote recorder, such as a personal computer or other external device. Additionally, the user may adjust the alarm settings, as conditions require.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

What is claimed is:

1. An air purification unit, comprising:
   a filter section, comprising:
      an air inlet on a first end,
      a rigidly framed filter inside said filter section and attached to said filter section on said first end such that the rigid frame is sealed with respect to said air inlet such that the only available flow path through said filter section is through said filter, and
      a fan coupling extending from a second end of said filter section; and
   a blower section, comprising:
      an air outlet, and
      an internally mounted motor and fan, said fan being configured to provide a pressure differential boundary between a high pressure on a discharge side of the fan and a low pressure on an inlet side of the fan when said fan is in operation,
         wherein the fan coupling of said filter section extends sufficiently into said blower section when said filter section is joined to said blower section such that the pressure differential boundary of said fan is no further downstream than the free end of said fan coupling
         and wherein the fan coupling is configured such that a section joining interface between said filter section and said blower section is located on the high pressure side of said pressure differential boundary such that risk of ingress of contaminated air from exterior of the air purification unit in the event of an imperfect seal at the section joining interface between said filter section and said blower section is eliminated.

2. The air purification unit of claim 1, said filter section further comprising a rigid outer shell.

3. The air purification unit of claim 1, said filter section further comprising an inlet section configured to receive a flexible hose or conduit.

4. The air purification unit of claim 3, wherein the inlet section further comprises an inlet coupling.

5. The air purification unit of claim 3, wherein the inlet section is integrated as a single unit with said filter section.

6. The air purification unit of claim 3, wherein the inlet section is sealingly attached to said filter section.

7. The air purification unit of claim 1, said blower section further comprising a rigid outer shell.

8. The air purification unit of claim 1, wherein said air outlet is configured to receive a flexible hose or conduit.

9. The air purification unit of claim 1, further comprising at least one clamp to connect said filter section to said blower section.

10. The air purification unit of claim 1, further comprising a control panel accessible from the exterior of said blower section.

* * * * *